(12) United States Patent
Whelan et al.

(10) Patent No.: US 6,279,404 B1
(45) Date of Patent: Aug. 28, 2001

(54) DEVICE AND METHOD FOR MEASURING DEFORMATION OF A MECHANICAL TEST SPECIMEN

(75) Inventors: Maurice Whelan, Angera; Alfredo C. Lucia, Osmate, both of (IT)

(73) Assignee: European Atomic Energy Community (EUROTOM), Luxembourg (LU)

( * ) Notice: Subject to any disclaimer, the term of this patent is extended or adjusted under 35 U.S.C. 154(b) by 0 days.

(21) Appl. No.: 09/463,263

(22) PCT Filed: Jul. 20, 1998

(86) PCT No.: PCT/EP98/04531

§ 371 Date: Apr. 14, 2000

§ 102(e) Date: Apr. 14, 2000

(87) PCT Pub. No.: WO99/05472

PCT Pub. Date: Feb. 4, 1999

(30) Foreign Application Priority Data

Jul. 21, 1997 (EP) .................................... 97830375

(51) Int. Cl.⁷ .................................................. G01L 1/24
(52) U.S. Cl. ................................. 73/800; 356/357
(58) Field of Search ............................. 73/800; 365/35.5, 365/32, 357

(56) References Cited

U.S. PATENT DOCUMENTS

| | | | |
|---|---|---|---|
| 4,280,764 | * 7/1981 | Sica, Jr. et al. | 356/35.5 |
| 4,286,879 | * 9/1981 | Jager et al. | 356/385 |
| 4,381,676 | * 5/1983 | Kaule et al. | 73/653 |
| 4,690,001 | * 9/1987 | Harvey et al. | 73/800 |
| 5,202,939 | * 4/1993 | Belleville et al. | 356/12 |
| 6,128,082 | * 10/2000 | Cloud | 356/357 |

FOREIGN PATENT DOCUMENTS 1 215 292 * 3/1987 (EP) .

* cited by examiner

*Primary Examiner*—Max Noori
(74) *Attorney, Agent, or Firm*—Frost Brown Todd LLC

(57) ABSTRACT

A device for measuring the deformation of a mechanical test specimen, and including a pressing member (3) for stressing a substantially flat specimen (16) in controlled manner by means of a punch (25); a Michelson interferometer having an optical branch (9d) defined optically by a first face (16b) of the specimen (16), and for generating interference images related to the deformation of the specimen (16); a telecamera (44) for acquiring and digitizing the interference images; and a processor (27) for processing the digitized images and controlling the measuring process fully automatically. The interferometer (9) may alternatively perform white light interferometry measurements, ESPI measurements, or ESPI profilometry measurements, by simply substituting the light source and control software.

13 Claims, 2 Drawing Sheets

DEVICE AND METHOD FOR MEASURING DEFORMATION OF A MECHANICAL TEST SPECIMEN

TECHNICAL FIELD

The present invention relates to a device and method for measuring deformation of a mechanical test specimen.

BACKGROUND ART

Mechanical tests performed on specimens of new material—such as hardness, breaking, plasticity or elasticity tests—are governed by ISO international standards, which, for the test to be considered valid, require a minimum specimen size. In some cases, however, as in the case of materials produced in nuclear reactors or particle accelerators, the amount of raw material produced may not be sufficient to form specimens of the prescribed ISO standard size.

By way of a solution to the problem, various nonstandard test methods have been devised for small-size specimens, most of which reproduce the standard methods on a smaller scale.

Particularly interesting nonstandard methods are those for testing disk-shaped specimens of 2–10 mm diameter and 0.1–1 mm thickness. A typical example is the so-called "punch test", wherein a concentrated load is applied to the central portion of a disk-shaped specimen secured about its peripheral edge, and deformation of the disk is measured to determine the mechanical characteristics, e.g. resistance, ductility, hardness and anelastic performance, of the material. The same type of test conducted up to the breaking point of the specimen provides for studying the fracture formation process prior to breakage.

Measurements of the above type, however, involve several problems, precisely on account of the small size of the specimen. That is, in addition to the difficulty encountered in securing the specimen firmly about its peripheral edge and applying the load in the exact center of the specimen, deformation of the specimen following application of the load is also difficult to measure to the required degree of resolution. Moreover, during application of the load, the small size of the specimen also produces end effects which may affect the reliability of the results.

The amount of deformation of the specimen is traditionally determined using known mechanical measuring devices, which, however, are limited as regards resolution and precision. Deformation of the specimen during testing may also be real-time controlled using optical image acquisition devices, such as a telecamera. In this case, however, the information supplied is difficult to process.

DISCLOSURE OF INVENTION

It is an object of the present invention to provide a deformation measuring device which may be used to advantage for mechanically testing small-size specimens, and more specifically for punch testing, and which provides for eliminating the aforementioned drawbacks.

According to the present invention, there is provided a device for measuring the deformation of a mechanical test specimen, as claimed in claim 1.

The present invention also relates to a method of measuring the deformation of a mechanical test specimen using the above device.

According to the present invention, there is provided a method of measuring the deformation of a mechanical test specimen, as claimed in claim 10.

BRIEF DESCRIPTION OF THE DRAWINGS

A preferred, non-limiting embodiment of the present invention will be described by way of example with reference to the accompanying drawings, in which.

BEST MODE FOR CARRYING OUT THE INVENTION

Figure 1A:
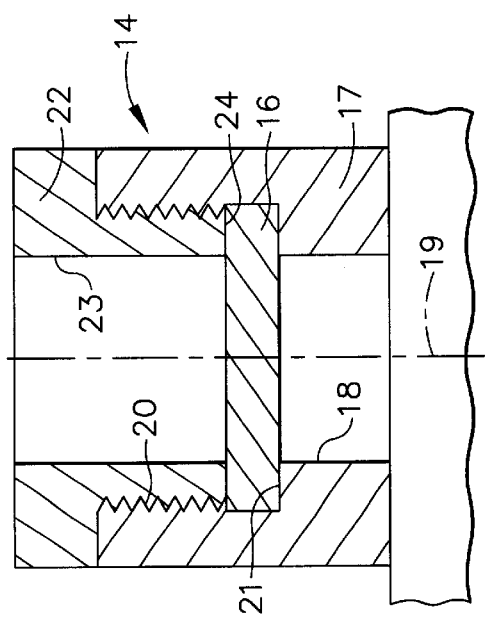
FIG. 1 shows a schematic front view of a device in accordance with the present invention.
Figure 1:
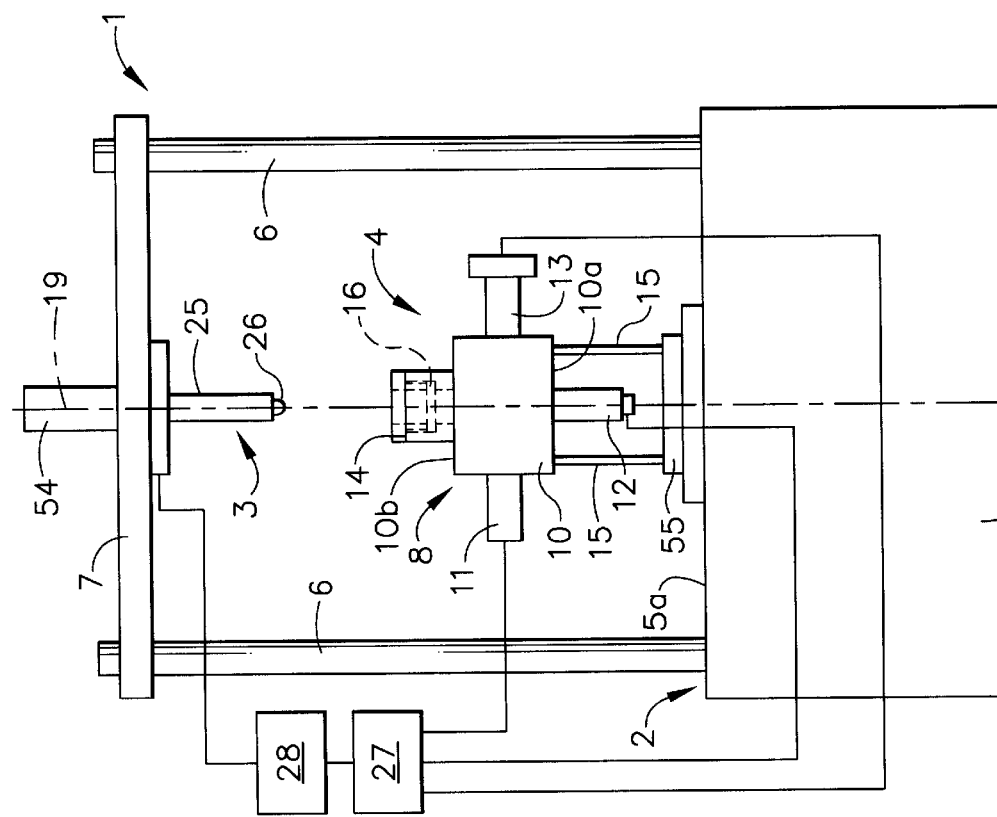

Number 1 in FIG. 1 indicates a device for mechanically testing small-size disk-shaped specimens, and more specifically, a punch test device.

Device 1 comprises a supporting structure 2; a mechanical pressing member 3; and an optical deformation detecting device 4.

Supporting structure 2 comprises a substantially parallelepiped base 5; two parallel uprights 6 extending perpendicularly from a wall 5a of base 5; and a straight crosspiece 7 supported on uprights 6 and facing wall 5a.

Optical device 4 is fitted to wall 5a, and comprises a support casing 8 located centrally between uprights 6 and housing an interferometer 9 (described later on with reference to FIG. 2). Casing 8 comprises a substantially cube-shaped central portion 10; and four appendixes 11, 12, 13, 14 extending from two pairs of opposite walls and in four directions perpendicular in pairs and in the same vertical plane.

Central portion 10 is supported on vertical rod-like elements 15 extending between a flat supporting element 16 fitted to wall 5a, and a bottom wall 10a of central portion 10 facing wall Sa, so that optical device 4 is raised with respect to base 5.

Appendix 14 extends from a top wall 10b, opposite wall 10a, towards crosspiece .7, and houses a mechanical test specimen 16; while appendixes 11, 12, 13 house component parts of interferometer 9.

More specifically, appendix 14 is tubular, and comprises a first tubular portion 17 extending perpendicularly to wall 10b and defining internally a first cylindrical cavity 18 coaxial with an axis. 19 and communicating with the inside of casing 8, and a second cylindrical cavity 20 coaxial with axis 19 and larger in diameter than first cavity 18. Between cavities 18 and 20, first tubular portion 17 therefore defines an annular shoulder 21 on which rests the peripheral edge of specimen 16 housed inside second cavity 20. Appendix 14 also comprises a second tubular portion 22 partially housed inside second cavity 20, connected to first tubular portion 17 by a threaded coupling, and defining a through hole 23 coaxial with axis 19. More specifically, second tubular portion 22 comprises an annular end edge 24 for pressing specimen 16 against shoulder 21; and, when interposed between first and second tubular portions 17 and 22, specimen 16 is positioned perpendicular to and centrally with respect to axis 19, and is locked axially between shoulder 21 and annular edge 24.

Pressing member 3 is fitted to the bottom of crosspiece 7, and comprises a cylindrical punch 25 fitted on the end with a ceramic ball 26 smaller in diameter than hole 23. Punch 25 extends along axis 19, is movable, along axis 19, to and from appendix 14 by means of a linear (e.g. pneumatic) actuator 54 fitted to crosspiece 7, and engages hole 23 in appendix 14 to position ball 26 against the face 16a of specimen 16 facing outwards of appendix 14, and so exert a controlled concentrated load on face 16a.

Linear actuator 54 and optical device 4 are controlled by a processor 27, which provides for controlling all the punch test operations automatically. More specifically, linear actuator 54 is controlled by a control unit 28 connected to processor 27 by a serial or GPIB interface.

Figure 2:
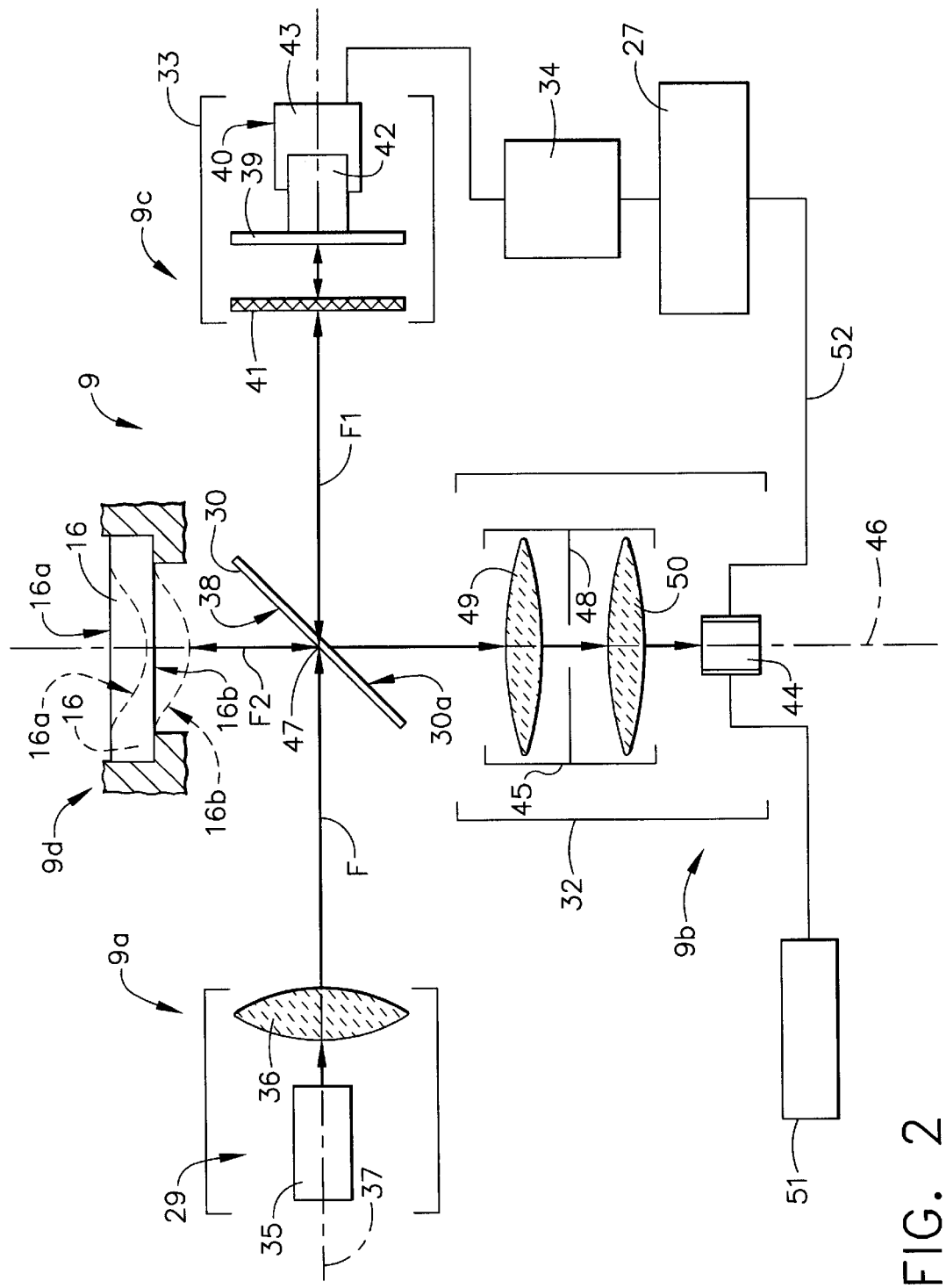
FIG. 2 shows a schematic view of part of the FIG. 1 device.

Optical interferometer 9, described later on with reference to FIG. 2, is a Michelson type, and may operate alternatively as a white light interferometer (using the also so-called "coherence radar" technique), or for ESPI (Electronic Speckle Pattern Interferometry) measurements, or for ESPI profilometry measurements by simply substituting the light source and control software of processor 27. The above three techniques are complementary, supply information relative to the shape of the specimen during and after application of the load, and, as is known, are characterized by different speeds and resolutions, so that one may be used in preference to another according to the characteristics of the specimen and the results expected.

With reference to FIG. 2, interferometer 9 comprises a first branch 9a in turn comprising a beam source 29 (housed in appendix .11) and a beam splitter 30 (housed in central portion 10) receiving a beam F from source 29; a second branch 9b in turn comprising a viewing device. 32 (housed in appendix 12) cooperating with beam splitter 30 and connected at the output to processor 27; a third branch 9c in turn comprising a reflecting device 33 (housed in appendix 13) also cooperating with beam divider 30 and driven by a drive circuit 34 connected to processor 27; and a fourth branch 9d in turn comprising specimen 16 housed in appendix 14.

More specifically, branch 9d may be defined optically by a mirror (not shown) in place of specimen 16 for regulating interferometer 9, or by specimen 16 itself, the bottom face 16b of which defines a retrodiffusion surface for the light from beam divider 30.

Beam source 29 comprises a light source 35, and a collimation system 36 in turn comprising a biconvex lens. Light source .35 conveniently comprises a low-coherence source (e.g. a superluminescent diode with a coherence length of a few microns) for white light interferometer measurements, or a high-coherence source (e.g. a laser with a coherence length of at least a centimeter) for ESPI or ESPI profilometry measurements. For ESPI profilometry measurements, the light emitted by source 35 must be either frequency adjustable or comprise two superimposed components of different frequencies. The light source is controlled by a drive and supply circuit (not shown), which may be connected to processor 27 for automatically controlling the frequency and intensity of the light emitted.

Collimation system 36 receives the light rays produced by source 35, and generates output beam F, which comprises rays substantially parallel to an optical axis 37.

Beam splitter 30 is of known type, and is located along optical axis 37 to receive beam F. More specifically, beam splitter 30 comprises a semireflecting surface 38 inclined at a 45° angle with respect to optical axis 37, so as to reflect part of beam F on to specimen 16 and transmit the rest of beam F to reflecting device 33.

Reflecting device 33 is located on the opposite side of beam splitter 30 to beam source 29, and comprises a flat reference mirror 39 crosswise to optical axis 37 and fitted to a position adjusting device 40 for moving mirror 39 along optical axis 37; and a filter 41 for adapting the light intensity of the beam reflected by mirror 39 to that of the beam reflected and diffused by specimen 16. More specifically, position adjusting device 40 comprises a piezoelectric actuator 42 with a resolution of about 1 nm and a dynamic range of about 50 microns, and which is fitted to a linear actuator 43 permitting controllable incremental steps of about 1 $\mu$m over a total range longer than 1 cm.

Viewing device 32 is located on the opposite side of beam splitter 30 to specimen 16, and comprises a telecamera 44, more specifically a black/white CCD (CHARGE COUPLED DEVICE) telecamera; and a focusing device 45 connected to telecamera 44 and facing beam splitter 30. Focusing device 45 has an optical axis 46 inclined 90° with respect to optical axis 37 and intersecting optical axis 37 at a point 47 on surface 38, and receives and focuses the light rays from beam splitter 30 on to the sensitive element (not shown) of telecamera 44. More specifically, focusing device 45 only focuses on to telecamera 44 the incoming rays parallel to optical axis 46.

In the FIG. 1 embodiment, focusing device 45 (shown schematically) comprises a diaphragm 48 crosswise to optical axis 46; and a pair of biconvex lenses 49, 50 crosswise to optical axis 46 and on either side of diaphragm 48. More specifically, lens 49 is positioned facing a face 30a of beam splitter 30 and at a focal distance $f_1$ from diaphragm 48; and lens 50 is positioned facing telecamera 44 and at a focal distance $f_2$ from diaphragm 48. Telecamera 44 also comprises a supply circuit 51, and is connected to processor 27 over a data line 52.

Device 1 operates as follows.

Before starting the test, interferometer 9 is set by inserting a mirror (not shown) in place of specimen 16, and, in known manner, aligning and correctly positioning the various optical components described above.

Once interferometer 9 has been set, specimen 16 is placed inside appendix 14, and, depending on the type of measurement involved (white light interferometry, ESPI or ESPI profilometry), the relative program is selected on processor 27, and optical device 4 is fitted with the necessary light source.

When the program is started, processor 27 supplies a signal to linear actuator 54 to move punch 25 down towards appendix 14, and, at the same time, interferometer 9 is activated. Ceramic ball 26 is therefore inserted inside hole 23 and positioned on to a central portion of face 16a of specimen 16, on which it exerts a controlled load to flex specimen 16 inwards of casing 8 and towards beam splitter 30. More specifically, and as shown schematically in FIG. 2, specimen 16 (shown by the continuous line in the undeformed position) is so stressed that a central portion is deformed axially (as shown by the dotted line) with respect to the peripheral portion, and defines a bulge extending towards beam splitter 30.

Figure 3:
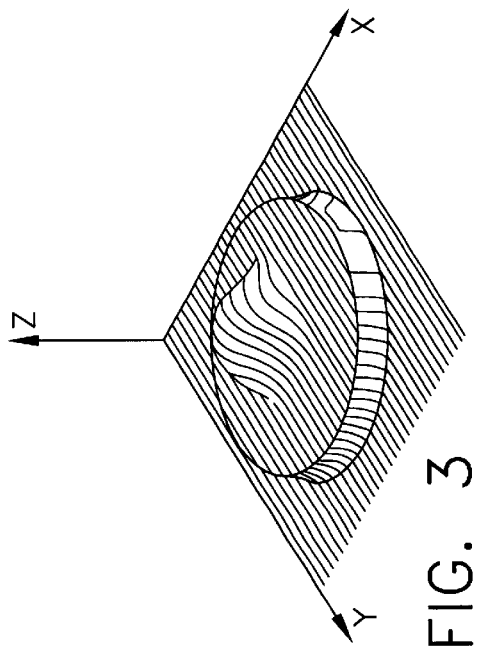
FIG. 3 shows the result of a deformation measurement made using the FIG. 1 device.

Interference images related instant by instant to the configuration of specimen 16 are generated on the sensitive element of telecamera 44 in known manner for each of the three measuring techniques mentioned above. Briefly, the interference images are formed as follows. Beam F produced by light source 35 impinges on beam splitter 30; and a first fraction F1 of beam F travels through surface 38, and impinges on reference mirror 39 by which first fraction F1 is reflected back to beam splitter 30. The phase of the reflected portion depends on the axial position assumed instant by instant by mirror 39, which is moved in known manner by piezoelectric actuator 42 or linear actuator 43 in steps of predetermined length and within a predetermined range according to the type of measurement involved. More specifically, the possibility of moving mirror 39 in submicrometric steps enables performance of the known "phase shifting" technique, which, by virtue of a known "phase unwrapping" algorithm in the processing software, provides for obtaining more three-dimensional information about the deformed specimen. First fraction F1 is then reflected by surface 30*a* towards focusing device 45 by which it is focused on to telecamera 44. A second fraction F2 of beam F is reflected by surface 38 on to specimen 16, is retrodiffused by face 16*b*,: and is sent, together with first fraction F1, to telecamera 44 where first and second fractions F1 and F2 are acquired in the form of interference images. Depending on the type of software for the test being performed, the interference images are processed to obtain three-dimensional images of the type shown in FIG. 3, which clearly shows, both qualitatively and quantitatively, the amount of deformation incurred. The same data, processed differently, provides for obtaining different spatial representations of the specimen, from which to obtain various types of information, such as offset of the load with respect to the center of face 16*b*, due, for example, to specimen 16 not being centered accurately with respect to axis 19.

The resolutions obtainable with the above type of measurement are about 10 nm (over a 3–5 $\mu$m range) for ESPI measurements, and 1 $\mu$m (over a range of tens of millimeters) for white light interferometry measurements. In the case of ESPI profilometry measurements, resolution and dynamic range depend on the pair of frequencies selected for the light emitted by source 35.

The advantages of the device and method according to the present invention are as follows.

As compared with known techniques, the measuring method described provides for obtaining better quantitative results, especially in terms of precision and resolution, and is more reliable.

Unlike conventional measuring techniques, the method described supplies information relative to the whole surface, as opposed to only the center, of the specimen, and relative to the overall deformation process, as opposed to only the end result. Moreover, detailed information is also obtained relative to the curvature and profile of the surface, and, by means of straightforward calculations, the stress within the structure of the material may be determined.

The method described also provides for determining any defects or nonuniformity, and for rapidly identifying any break regions in the specimen during testing.

The choice of three different types of measurement, each supplying different information according to the type of test specimen, provides for more versatile, more accurate measurement; and the switch from one type of measurement to another is made extremely easily and quickly.

Finally, as stated, the method described is fully automatic, and supplies the operator directly at the output with data relative to the deformed specimen.

Clearly, changes may be made to the method and optical measuring device as described and illustrated herein without, however, departing from the scope of the present invention.

In particular, light source 35 may be located outside casing 8, in which case, the light emitted is directed into casing 8 by an optical fiber.

Also, an integrated test and measuring device may be formed, wherein the optical and mechanical actuating parts are housed in one structure also housing the specimen.

What is claimed is:

1. A device for measuring the deformation of a mechanical test specimen, characterized by comprising:

a supporting means (14, 21, 24) for supporting said specimen (16); said specimen being generally flat and being defined by at least a substantially flat first face (16*b*);

a pressing member (3) movable by actuating means (54) with respect to said supporting means (14, 21, 24) for stressing said specimen (16) in a controlled manner and exerting a controlled concentrated force on the face of the specimen (16) deforming mainly the portion of the specimen where said concentrated force is applied; and an interferometer (9) comprising a branch (9*d*) defined optically by said first face (16*b*) of said specimen (16) and for generating interference images related to the deformation of said specimen (16).

2. A device as claimed in claim 1, characterized by also comprising:

image acquisition means (44) for acquiring images from said interferometer (9) and for acquiring and digitizing said interference images; and image processing means (27) connected to said image acquisition means (44) and for processing said acquired and digitized images.

3. A device as claimed in claim 1 or 2, characterized in that said pressing member (3) comprises an elongated element (25) movable axially along an axis (19) substantially perpendicular to said specimen (16).

4. A device as claimed in any one of the foregoing claims from 1 to 3, characterized by comprising a casing (8) supporting said interferometer (9); said casing (8) also comprising said supporting means (14, 21, 24) for supporting said specimen (16).

5. A device as claimed in claim 4, characterized in that said supporting means (14, 21, 24) comprise a tubular appendix (14) housing said specimen (16) and extending from a central portion (10) of said casing (8).

6. A device as claimed in any one of the foregoing claims, characterized by comprising a supporting structure (2) in turn comprising a base (5) for supporting said interferometer (9), and an upper supporting element (7) spaced with respect to said base (5) and facing said base (5); said upper supporting element supporting said pressing member (3) and said actuating means (54).

7. A device as claimed in any one of the foregoing claims, characterized in that said interferometer (9) comprises a Michelson interferometer in turn comprising:

a light source (29) for generating a light beam (F) traveling along a supply branch (9*a*);

beam splitting means (30) receiving said light beam (F) generated by said light source (35), and generating a first (F2) and a second (F1) light beam;

a measuring branch (9*d*) comprising said specimen (16), and for receiving and reflecting said first light beam (F2) on to said beam splitting means (30);

a reference branch (9*c*) comprising reflecting means (39) for receiving and reflecting said second light beam (F1) on to said beam splitting means (30); and an acquisition branch (9*b*) comprising image acquisition means (44) for receiving said first light beam (F2) reflected by said specimen (16) and said second light beam (F1) reflected by said reflecting means (39).

8. A device as claimed in claim 7, characterized by comprising shift means (40) connected to said reflecting means (39) and for translating the reflecting means (39) in controlled manner.

9. A device as claimed in any one of the foregoing claims, characterized in that said light source (35) may be selected from the group comprising:
- a low-coherence source for white light interferometry measurements;
- a high-coherence source with a single nonadjustable frequency for ESPI measurements; and
- a high-coherence source with two non-adjustable frequencies or a single adjustable frequency for ESPI profilometry measurements.

10. A method for measuring the deformation of a mechanical test specimen, said specimen (16) being generally flat, and being defined by at least a substantially flat first face (16b); characterized by comprising the steps of:
- directing a first light beam (F2) onto said first face (16b) of said specimen (16) and acquiring (40) the reflected beam;
- producing interference between said reflected beam and a reference beam (F2) to obtain interference images;
- mechanically stressing the specimen (16) in a controlled manner by exerting a controlled concentrated force on a face of the specimen (16) deforming mainly the portion of the specimen (16) where the concentrated force is applied; and
- acquiring (44) and processing (27) said interference images to obtain information relative to the deformation of said specimen (16).

11. A method as claimed in claim 10, characterized in that said step of mechanically stressing said specimen (16) comprises the step of applying a controlled concentrated load on a second face (16a) of said specimen (16).

12. A method as claimed in claim 10 or 11, characterized by also comprising a preliminary step wherein a peripheral portion of said specimen (16) is mated stably with retaining means (21, 24); said step of stressing said specimen (16) comprising the step of moving a pressing member (3) with respect to said retaining means (21, 24) and towards said specimen (16) to produce said deformation.

13. A method as claimed in any one of the foregoing claims from 10 to 12, characterized by comprising the steps of:
- generating an input light beam (F);
- dividing said input light beam (F) to generate said first light beam (F2) and a second light beam (F1);
- directing said second light beam (F1) on to reflecting means (39) to form a second reflected light beam defining said reference beam.

* * * * *

UNITED STATES PATENT AND TRADEMARK OFFICE
CERTIFICATE OF CORRECTION

PATENT NO.   : 6,279,404 B1
DATED        : August 28, 2001
INVENTOR(S)  : Maurice Whelan and Alfredo C. Lucia Page 1 of 1

It is certified that error appears in the above-identified patent and that said Letters Patent is hereby corrected as shown below:

Column 2,
Line 8, please insert -- Figure 1A shows a blown-up schematic view of the specimen-holding portion of the present invention. --

Signed and Sealed this

Ninth Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,279,404 B1  
DATED         : August 28, 2001  
INVENTOR(S)   : Maurice Whelan and Alfredo C. Lucia It is certified that error appears in the above-identified patent and that said Letters Patent is hereby corrected as shown below:

<u>Title page,</u>
Item [73], Assignee, "European Atomic Energy Community, (EUROTOM), Luxembourg (LU)" should read -- European Atomic Energy Community (EURATOM), Luxembourg (LU) --

Signed and Sealed this

Twenty-fourth Day of December, 2002

JAMES E. ROGAN  
*Director of the United States Patent and Trademark Office*